United States Patent
Guthrie et al.

(10) Patent No.: US 9,924,901 B2
(45) Date of Patent: Mar. 27, 2018

(54) METHODS, MEDIA, AND APPARATUS FOR OPTIMIZING PHYSICAL TRAINING BASED ON REAL-TIME BLOOD LACTATE MONITORING

(71) Applicant: Potomac Health Solutions, Inc., Oak Hill, VA (US)

(72) Inventors: Paul Joseph Guthrie, Washington, DC (US); Kenneth Jay Gordon, Oak Hill, VA (US)

(73) Assignee: Potomac Health Solutions, Inc., Reston, VA (US)

( * ) Notice: Subject to any disclaimer, the term of this patent is extended or adjusted under 35 U.S.C. 154(b) by 56 days.

(21) Appl. No.: 14/739,964

(22) Filed: Jun. 15, 2015

(65) Prior Publication Data
US 2015/0359480 A1   Dec. 17, 2015

Related U.S. Application Data

(60) Provisional application No. 62/012,831, filed on Jun. 16, 2014.

(51) Int. Cl.
| | | |
|---|---|---|
| *A61B 5/02* | (2006.01) | |
| *A61B 5/00* | (2006.01) | |
| *A61B 5/145* | (2006.01) | |
| *A61B 5/1455* | (2006.01) | |
| *G09B 19/00* | (2006.01) | |
| *A61B 5/0205* | (2006.01) | |
| *A61B 5/024* | (2006.01) | |
| *A61B 5/08* | (2006.01) | |
| *A61B 5/083* | (2006.01) | |

(52) U.S. Cl.
CPC .......... *A61B 5/4866* (2013.01); *A61B 5/1455* (2013.01); *A61B 5/14546* (2013.01); *G09B 19/0038* (2013.01); *A61B 5/0205* (2013.01); *A61B 5/02438* (2013.01); *A61B 5/0816* (2013.01); *A61B 5/0836* (2013.01); *A61B 5/4833* (2013.01); *A61B 5/7264* (2013.01); *A61B 2503/10* (2013.01)

(58) Field of Classification Search
None
See application file for complete search history.

(56) References Cited

U.S. PATENT DOCUMENTS

| | | |
|---|---|---|
| 5,757,002 A | 5/1998 | Yamasaki et al. |
| 6,687,535 B2 | 2/2004 | Hautala et al. |
| (Continued) | | |

FOREIGN PATENT DOCUMENTS

WO   WO 2014/025430 A2   2/2014

OTHER PUBLICATIONS

International Search Report and Written Opinion for International Patent Application No. PCT/US2015/035794, dated Sep. 15, 2015.

*Primary Examiner* — Ankit D Tejani
(74) *Attorney, Agent, or Firm* — Cooley LLP

(57) ABSTRACT

Some embodiments described herein relate to receiving lactate concentration data from a non-invasive sensor. A ratio of aerobic to anaerobic exertion can be determined based on the concentration of lactate, and real-time feedback can be provided based on the ratio of aerobic to anaerobic exertion. For example, the user can be encouraged to maintain a level of intensity in which he or she approaches (but does not exceed) maximal oxygen consumption.

33 Claims, 2 Drawing Sheets

(56) References Cited

U.S. PATENT DOCUMENTS

| | | | |
|---|---|---|---|
| 6,736,759 B1 | 5/2004 | Stubbs et al. | |
| 7,149,568 B2 | 12/2006 | Amano et al. | |
| 7,272,499 B2 | 9/2007 | Grenfell et al. | |
| 7,384,376 B2 | 6/2008 | Maschke | |
| 7,715,982 B2 | 5/2010 | Grenfell et al. | |
| 7,740,589 B2 | 6/2010 | Maschke et al. | |
| 8,105,208 B2 | 1/2012 | Oleson et al. | |
| 8,200,323 B2 | 6/2012 | DiBenedetto et al. | |
| 8,229,532 B2 | 7/2012 | Davis | |
| 8,465,397 B2 | 6/2013 | Saalasti et al. | |
| 8,579,767 B2 | 11/2013 | Ellis et al. | |
| 8,647,270 B2 | 2/2014 | LeBoeuf et al. | |
| 8,652,009 B2 | 2/2014 | Ellis et al. | |
| 8,652,010 B2 | 2/2014 | Ellis et al. | |
| 8,694,136 B2 | 4/2014 | Ellis et al. | |
| 8,721,502 B2 | 5/2014 | Ellis et al. | |
| 8,740,752 B2 | 6/2014 | Ellis et al. | |
| 8,768,489 B2 | 7/2014 | Thieberger et al. | |
| 8,784,115 B1 | 7/2014 | Chuang | |
| 8,801,577 B2 | 8/2014 | Dibenedetto et al. | |
| 8,814,755 B2 | 8/2014 | Ellis et al. | |
| 8,823,524 B2 | 9/2014 | Bradley et al. | |
| 8,827,869 B2 | 9/2014 | Ellis et al. | |
| 8,855,756 B2 | 10/2014 | DiBenedetto et al. | |
| 8,894,548 B2 | 11/2014 | Ellis et al. | |
| 8,923,998 B2 | 12/2014 | Ellis et al. | |
| 2008/0300498 A1* | 12/2008 | Edwards | A61B 5/024 600/520 |
| 2009/0024013 A1* | 1/2009 | Soller | A61B 5/14551 600/324 |
| 2010/0049016 A1 | 2/2010 | Aronowitz et al. | |
| 2013/0096396 A1* | 4/2013 | Riedel | A61B 5/0205 600/301 |
| 2013/0096401 A1 | 4/2013 | Lash et al. | |

\* cited by examiner

Fig. 3

| Notional training zones and effects for an individual | | | |
|---|---|---|---|
| Heart rate | Zone | Effect | Lactate (mm/l) |
| 185+ | 6 | Lactic acid buffering | > 6.0 |
| 178 | 5 | Anerobic threshold | 4.0 to 6.0 |
| 165 | 4 | High intensity endurance | 3.0 to 4.0 |
| 155 | 3 | Endurance | 3.0 to 4.0 |
| 145 | 2 | Oxygen uptake | <2.0 |
| 120 | 1 | Recovery | <2.0 |

Fig. 4

| Workout Summary | | | |
|---|---|---|---|
| | Goal | Actual | Compliance |
| Zone 1: | 40:00 | 55:34 | +15:34 |
| Zone 2: | 20:00 | 7:28 | -12:32 |
| Zone 3: | 0:00 | 1:12 | +1:12 |
| Zone 4: | 7:30 | 8:44 | +1:14 |
| Zone 5: | 0:00 | 0:27 | +0:27 |
| Zone 6: | 0:00 | 0:07 | +0:07 |

| Weekly Training Report | | | |
|---|---|---|---|
| | Goal | Actual | Remaining |
| Zone 1: | 240:00 | 232:12 | 7:48 |
| Zone 2: | 120:00 | 60:54 | 59:06 |
| Zone 3: | 0:00 | 4:56 | 0:00 |
| Zone 4: | 45:00 | 46:45 | 0:00 |
| Zone 5: | 0:00 | 3:34 | 0:00 |
| Zone 6: | 0:00 | 0:44 | 0:00 |

METHODS, MEDIA, AND APPARATUS FOR OPTIMIZING PHYSICAL TRAINING BASED ON REAL-TIME BLOOD LACTATE MONITORING

CROSS REFERENCE TO RELATED APPLICATIONS

This application claims the benefit of provisional U.S. Patent Application No. 62/012,831, filed Jun. 16, 2014, under 35 U.S.C. § 119(e), the disclosure of which is hereby incorporated by reference in its entirety.

BACKGROUND

This application relates generally to real-time monitoring of a user's blood lactate (also referred to lactic acid) concentration during a physical activity and providing training guidance to that user during the physical activity. Methods, media, and apparatus that can increase training efficiency by providing real-time feedback based on lactate concentration are described herein.

"Getting fit" is a perennial New Year's resolution. The availability of a wide range of exercise equipment, training aids, and fitness magazines bears testament to the basic fact that some training methods are more effective than others. Even when an individual seeks to increase his or her fitness, the effectiveness of training can be compromised if the user engages in a training regimen that was not specifically designed for that individual and/or by deviations from the training protocol. Elite athletes have long benefited from coaches and training staffs that carefully monitor training regimens and adjust exertion goals based on performance.

Training responses vary at different levels of intensity. Because the human body uses multiple energy systems for fueling output, including aerobic and anaerobic metabolism, training efficiency can be improved by targeting specific energy systems for specific durations. Elite and amateur athletes alike can improve the efficiency of their workouts by conforming their workouts to structured training regimens, which may prescribe target intensity, target duration, and/or a sequence of different intensities.

Developing a structured training regimen for a particular individual and/or accurately conforming a workout to a structured training regimen requires insight into the body's function. Several indicators can be used as proxies for measuring exertion, including heart rate, levels of carbon dioxide exhaled, and concentrations of lactate in the blood. Heart rate, however, is an unreliable indicator of exertion activity with high latency. Carbon dioxide measurements require specialized exercise lab equipment. Lactate concentration is an excellent proxy for exertion, but has historically not been available in real-time and/or without drawing blood. A need therefore exists for methods, media, and apparatus for optimizing physical training based on real-time blood lactate monitoring.

SUMMARY

Some embodiments described herein relate to receiving lactate concentration data from a non-invasive sensor. A ratio of aerobic to anaerobic exertion can be determined based on the concentration of lactate, and real-time feedback can be provided based on the ratio of aerobic to anaerobic exertion. For example, the user can be encouraged to maintain a level of intensity in which he or she approaches (but does not exceed) maximal oxygen consumption.

BRIEF DESCRIPTION OF THE DRAWINGS

FIG. 3 is an example chart of various target training zones.

FIG. 4 is an example chart of a workout summary.

DETAILED DESCRIPTION

Figure 1:
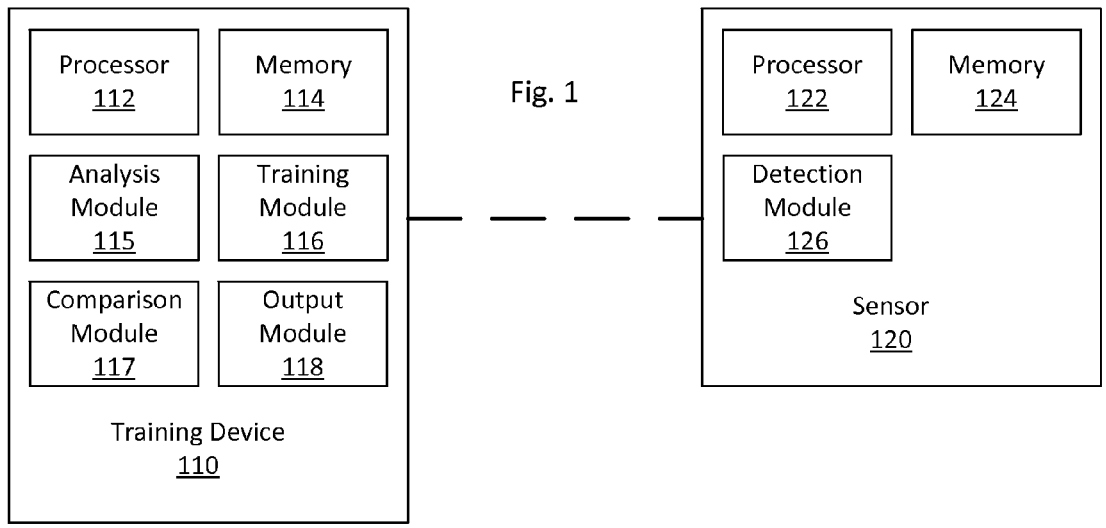
FIG. 1 is a schematic block diagram of a system for providing real-time feedback on physical training based on lactate concentration, according to an embodiment.

Mammals have multiple energy systems, including aerobic metabolism and anaerobic metabolism. When muscles are well oxygenated, they preferentially produce energy via aerobic metabolism. As the intensity of a physical activity increases, the supply of oxygen drops and a larger portion of the energy produced to engage in the physical activity is generated via anaerobic activity, a byproduct of which is lactate. As the intensity of physical activity decreases, well oxygenated muscles quickly oxidize lactate to form pyruvate, decreasing lactate concentration. Blood lactate concentration is therefore an excellent indicator of the current ratio of aerobic to anaerobic metabolism occurring in a mammalian body.

Some embodiments described herein relate to receiving lactate concentration data from a non-invasive sensor. A ratio of aerobic to anaerobic exertion can be determined based on the concentration of lactate, and real-time feedback can be provided based on the ratio of aerobic to anaerobic exertion. For example, the user can be encouraged to maintain a level of intensity in which he or she approaches (but does not exceed) maximal oxygen consumption.

Some embodiments described herein relate to an apparatus having an input module that can be receive data from a non-invasive lactate concentration sensor. A training module can be coupled to the input module and configured to calculate an exertion level based on the lactate concentration. An output module can be communicatively coupled to the training module and configured to cause an output device to provide training feedback while a user is engaged in physical activity.

Some embodiments described herein relate to classifying a training zone for a physical activity based on a lactate concentration while the physical activity is occurring. If the training zone is higher than a target training zone, the user can be prompted, in-real time, to reduce an intensity of the physical activity. Conversely, if the training zone is lower than the target zone, the user can be prompted to increase intensity of the physical activity.

The efficiency of training can be improved by targeting exercising to precise intensity levels to systematically engage different energy systems, sometimes referred to as "zone training." For example, many athletes practice interval training, in which relatively long periods of relatively low intensity aerobic exercise are punctuated by relatively short high-intensity exercises designed to recruit fast-twitch muscles and engage anaerobic metabolic pathways.

FIG. 3 shows relationships between notional training zones and lactate concentrations, which are highly correlated to the ratio of aerobic to anaerobic metabolism occurring within the body. Historically, zone training has relied on heart rate. Heart rate, however, is only indirectly and non-linearly correlated to the ratio of aerobic to anaerobic exercise. Because lactate is a direct product of anaerobic metabolism, it is a better indicator of how much anaerobic metabolism is occurring than heart rate. Effective training regimens based on real-time lactate concentration, however, have not previously been developed.

As described herein, "zone 2," is associated with oxygen uptake and very high ratios of aerobic to anaerobic metabolism. Once an athlete crosses the "aerobic threshold" into "zone 3," which, in humans, is typically associated with a blood lactate concentration of about 2.0 millimoles/liter (e.g., 1.8-2.2 millimoles/liter), muscles begin to supplement energy production demands with anaerobic metabolism. Therefore, maximizing an intensity of a physical activity without crossing the threshold into zone 3 causes muscles to function at near peak aerobic power. This is a highly efficient training strategy. Once an athlete transitions to zone 3, the effect of relatively low levels of anaerobic metabolism allows muscles to perform at less than peak aerobic capacity. Therefore, although the overall intensity of an exercise increases as the athlete transitions from zone 2 to zone 3, counterintuitively, training efficiency decreases. Accordingly, in some embodiments, training regimens described herein can target the "top" of zone 2. Similarly stated, for at least a portion of a workout, an athlete can be encouraged to maintain at an intensity close to, without exceeding the aerobic threshold. Similarly, highly efficient training can occur at the top of other suitable zone, such as at the top of zone 4, before the body crosses the "anaerobic threshold," which, in humans, is typically associated with a blood lactate concentration of about 4.0 millimoles per/liter (e.g., 3.8-4.2 millimoles/liter). Accordingly, in some embodiments, training regimens described herein can target the "top" of any suitable zone.

As shown in FIG. 3, heart rate can also be correlated to a training zone, but heart rate is generally a less reliable predictor of the ratio of aerobic to anaerobic exercise. In particular, heart rate is poor predictor of the threshold between zones 2 and 3. Therefore, it has historically not been possible to provide effective real-time training feedback to athletes wishing to target zone 2. Lactate, being a direct product of anaerobic metabolism, is an excellent indicator of the transition between zones 2 and 3.

Some embodiments described herein relate to targeting training intensity to maximize aerobic metabolism and minimize anaerobic metabolism. Because there are few or no cues that are perceptible to the athlete when low-level anaerobic metabolism begins to occur, unguided athletes attempting to engage in aerobic activity will frequently exercise at an intensity level that causes a relatively small but significant amount of anaerobic metabolism to occur. The occurrence of such anaerobic metabolism can be counterproductive to aerobic training. Known heart-rate monitor based training programs are ineffective at detecting the presence of such anaerobic metabolism. The lactate-based systems and methods described herein are sensitive to relatively small amounts of anaerobic exertion and are therefore suitable for increasing the efficiency of training, for example, by encouraging a user to maximize aerobic exercise without engaging significant anaerobic metabolism. Other training regimens described herein include targeting particular ratios of aerobic to anaerobic exercise for a particular duration or percentage of a workout and/or targeting particular zones in a particular order.

FIG. 1 is a schematic block diagram of a system for providing real-time feedback on physical training based on lactate concentration, according to an embodiment. The system includes a training device 110 communicatively coupled to a sensor 120. The training device 110 can be communicatively coupled to the sensor 120 via a wired connection and/or a wireless connection. In some embodiments, the training device 110 and the sensor 120 can be enclosed within a single housing, such as a wearable compute device. In other embodiments, the training device 110 and the sensor 120 can be stand-alone components communicatively coupled via USB®, Bluetooth®, or any other suitable communication mechanism and/or protocol. For example, and as described in further detail herein, the training device 110 can be a smart phone and the sensor 120 can be a body-worn device and/or incorporated into a clothing item.

The sensor 120 can be any suitable device for measuring blood lactate concentration. In some embodiments, the sensor 120 can be operable measure blood lactate concentration and send data associated with blood lactate concentration to the training device 110 in real-time. Similarly stated, the sensor 120 can be operable to detect and/or report lactate concentrations in the blood of a subject while the subject is performing a physical activity and/or report the lactate concentrations to the training device with substantially no delay (e.g., with a delay of less than 5 seconds, less than 1 second, less than 5 milliseconds, etc.).

The sensor 120 includes a processor 122, a memory 124, and a detection module 126. The detection module 126 can be any suitable hardware and/or software (stored in the memory 124 and/or executing on the processor 122) for measuring lactate and/or lactic acid concentrations and/or quantity. In some embodiments the entire sensor 120, including the detection module 126 can be non-invasive and/or may not require a blood sample. For example, the detection module 126 can be operable to transdermally detect lactate concentration using electropotential measurements (or other electromagnetic measurements) and/or optical measurements (e.g., by detecting photons (directly or as reflected) in one or more spectra such is visible light, near-infrared light, or infrared light).

The processor 122 can be for example, a general purpose processor, a Field Programmable Gate Array (FPGA), an Application Specific Integrated Circuit (ASIC), a Digital Signal Processor (DSP), and/or the like. The processor 122 can be configured to retrieve data from and/or write data to memory, e.g., the memory 124, which can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth.

The training device 110 can be a smart phone (e.g., an iPhone®, an Android® phone, etc.), a personal computer (e.g., a desktop, laptop, tablet, etc.) and/or any other suitable computing entity (e.g., custom hardware and/or software configured to provide training feedback). In some embodiments, the training device 110 can be carried and/or worn by the user. In other embodiments, the training device can be incorporated into athletic equipment, such as a running shoe, a ski, an oar, etc. In yet other embodiments, the training device 110 can be a remote computing entity configured to receive telemetry from the sensor 120 over a long-distance network, such as a cellular data network, the internet, etc. In some embodiments, the training device 110 can be used by a coach or trainer to monitor athletic activities performed by the wearer of the sensor 120.

The training device 110 includes a processor 112 and a memory 114, which can be functionally and/or structurally similar to the processor 122 and/or the memory 124, respectively. The training device 110 further includes an analysis module 115, a training module 116, a comparison module 117, and an output module 118.

The analysis module 115 can be hardware and/or software (stored in the memory 114 and/or executing on the processor 112) operable to receive and/or process lactate and/or lactic acid data received from the sensor 120. The analysis module 115 can be operable to receive and/or process lactate data in real time (e.g., while a physical activity is underway and/or with a delay of a delay of less than 5 seconds, less than 1 second, less than 5 milliseconds, etc.) and/or substantially continuously (e.g., updating every 10 seconds, every 5 seconds, every 1 second, every 10 milliseconds, etc.).

As described in further detail herein, the analysis module 115 can be operable to associated lactate data with an intensity of the physical activity. For example, the analysis module 115 can be operable to correlate lactate concentration to a quantity of anaerobic metabolism and/or a ratio of aerobic to anaerobic exercise. The analysis module 115 can assign a "zone" to the current activity based on lactate concentration, for example, based on the lactate concentrations shown in FIG. 3.

In some instances, the analysis module 115 can be operable to receive heart rate, respiration data, $CO_2$ exhalation data, and/or any other suitable physiological data (e.g., from the sensor 120 and/or any other suitable physiological sensor) and can assign a zone based on lactate concentration and any other suitable physiological data. For example, the analysis module 115 can be operable to distinguish between zones 1 and 2, which are both associated with very high ratios of aerobic to anaerobic exertion, based, at least in part, on heart rate.

The training module 116 can be hardware and/or software (stored in the memory 114 and/or executing on the processor 112) operable to define workout regimens for the user of the training device 110 and/or store training regimens (e.g., in the memory 114). For example, the training module 116 can be obtain and/or store pre-defined generic training regimens, for example from an internet repository. In some instances, the training module 116 can be operable to define one or more custom training regimens for the user based, for example, on the user's goals, and/or current and/or historic exercise data for the user.

The comparison module 117 can be hardware and/or software (stored in the memory 114 and/or executing on the processor 112) operatively coupled to the analysis module 115 and the training module 116, and can be operable to determine whether a current training zone (e.g., as determined by the analysis module 115) corresponds to a target zone. For example and as described in further detail herein, the training regimen (defined by the training module 116) can prescribe exercising in zone 2 for a period of time. Similarly, the training regimen can prescribe increasing the intensity to zone 4 (or any other suitable zone) at a particular time and for a particular duration (e.g., after 7 minutes of zone 2 exertion, 45 seconds of zone 4 exertion can be prescribed). As yet another example, the training regimen can prescribe that at least 85% of a workout should be at zone 2 intensity. The comparison module 117 can be operable to verify compliance with any and/or all such prescriptions. For example, the comparison module 117 can be operable to compare current exertion to current prescribed intensity, track time and history of an exercise, and/or verify that the user's intensity level changes when called for by the training regimen, etc.

The comparison module 117 can be operably coupled to the output module 115. The output module can be hardware and/or software (e.g., stored in memory 114 and/or executing on the processor 112) operable to cause user-perceptible signals to be generated. For example, the output module 115 can be operable to cause a visual output to be presented via a display device (e.g., a LCD screen, an e-ink display, etc.) an audible output to be presented via a speaker or other suitable device, a haptic, and/or any other suitable output to be presented. As described in further detail herein, the output module 115 can be operable to cause cues, feedback, encouragement, tracking data, and/or any other suitable information to be presented to the user to aid in adhering to the training regimen. For example, the output module 115 can be operable to encourage the user to increase and/or decrease the intensity of a physical activity when the user is not adhering to the training regimen.

Figure 2:
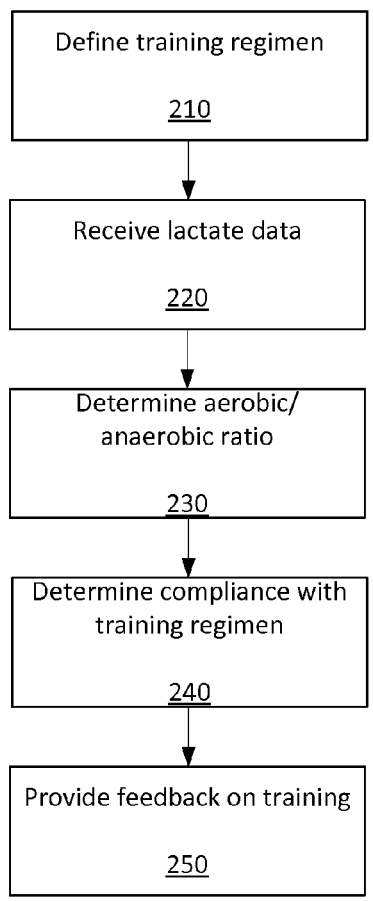
FIG. 2 is a flow chart of a method for providing training feedback based on lactate concentration, according to an embodiment.

FIG. 2 is a flow chart of a method for providing training feedback based on lactate concentration, according to an embodiment. At 210 a training regimen can be defined, for example, by the training module 116 shown and described above with reference to FIG. 1. The training regimen can specify the amount of time and/or the percent of time the athlete should stay in a particular training zone measured over the course of a workout, a week, a month, and/or a year. The prescribed amount and/or percent of time can be determined by an analysis of the athlete's relative strengths, the athlete's goals (e.g., lose a certain amount of weight, improve the time taken to complete an activity, etc.), an event for which the athlete is training (e.g., a race, a match, a game, etc.), the amount of time until the event, and so forth.

In some instances, the training regimen can be based on generally applicable zone thresholds, for example, as shown in FIG. 3. In other instances, the training regimen can be based on personalized zone thresholds. For example, defining the training regimen, at 210 can include one or more calibration exercises. As one example, the user can be encouraged to slowly increase the intensity of an exercise. As the user begins exercising, the analysis module 116 can define a baseline lactate concentration. As the intensity increases, the analysis module 116 can monitor the lactate concentration. When the lactate concentration deviates from the baseline lactate concentration, (e.g., when an inflection point in a lactate concentration curve is detected) the training module 116 can define the aerobic threshold, which is typically around 2.0 millimoles/liter. This personalized aerobic threshold can be used as the zone 2-zone 3 threshold for training regimens described in further detail herein. As another example, defining the training regimen, at 210, can include a calibration exercise designed to detect a personalized anaerobic threshold. The anaerobic threshold can be detected during a high-intensity exercise and can be associated with another change in slope or inflection point of lactate concentration indicative of lactate being produced by muscles engaged in anaerobic metabolism faster than the rest of the body can metabolize the produced lactate, which is typically around 4.0 milimoles/liter. This personalized anaerobic threshold can be used as the zone 4-zone 5 threshold for training regimens described in further detail herein. In some instances, calibration exercises can be repeated to confirm and/or improve the accuracy of the individualized aerobic threshold and/or anaerobic thresholds.

In some instances, defining a training regimen can include accessing a database (e.g., a local database, a remote database, a third party repository, crowd sourced data, etc.) of previously generated quantitative training programs for various events, distances, training goals, timeframes, etc. For example, In other instances, defining a training regimen can include defining a custom training regimen based on, for example, past records of physical activity, user-supplied goals, user-expressed training preferences, etc. Defining a training regimen can include calculating daily, weekly, monthly, and/or yearly training volume using, for example, principles of progressive loading and periodization, i.e., gradually increasing volume by week and by month, with rest weeks, and varying the types of zones appropriately within each of those cycles. This variation in types of zone can further include instruction to the user on the amounts of time spent in each zone, time spent in the aggregate, and the order in which the training zones are targeted. This time spent (and/or order spent in the zones) are applicable over the course of a single exercise session, and also across multiple/many sessions measured across timespans measured in days, weeks, and/or months.

Thus, in some instances, defining a training regimen, at 210 can include defining a long-term training regimen and/or selecting an individual workout from a long term training regimen. In other instances, defining a training regimen, at 210 can include defining a one-off training regimen for a single exercise session.

An example of a training regimen is shown in the "Goal" columns of FIG. 4. Such a training regimen can further include a specific sequence of intensities. For example, a workout may prescribe 18 minutes of zone 1 warm-up, followed by four repetitions of (1) 5 minutes of zone 2 activity, (2) 1.5 minutes of zone 4 high intensity activity, (3) 4 minutes of zone 1 cool down.

At 220, real-time lactate data can be received. Similarly stated, the training device 110 can receive a signal from a sensor 120, as shown and described above with reference to FIG. 1. In some instances, lactate concentration data can be received, at 220, in response to the user beginning a workout and/or in response to the user providing an input to the sensor 120 and/or the training device 110 indicating that the user is commencing a physical activity. In response to the lactate data being received, at 210, the analysis module 115 can be operable to determine a quantity of anaerobic metabolism and/or a ratio of aerobic to anaerobic metabolism, in real-time and/or substantially continuously, at 220. The lactate concentration received, at 220, (and hence the ratio of aerobic to anaerobic metabolism determined, at 230) can be suitable to provide leading indicators predictive of certain conditions such as (but not limited to) overtraining and injury before they happen.

Compliance with the training regimen can be determined, at 240. At 240, the comparison module 117 can, in real time and/or substantially continuously, compare lactate concentration received at 220 and/or the ratio of aerobic to anaerobic metabolism, determined, at 230, to the training regimen defined, at 210. For example, if the training regimen calls for the user to currently be exercising in zone 2, but the user is actually exercising with zone 3 intensity, the compliance module 117 can determine that the user is not complying with the training regimen, at 240. Similarly, if the training regimen calls for 8 minutes of zone 4 activity over the course of a workout (which may last, for example, for 45 minutes), the compliance module 117 can be operable to track the cumulative amount of time spent in zone 4 and can be operable to determine when the user exceeds 8 minutes of zone 4 activity. As yet another example, if the training regimen calls for 180 minutes of zone 2 activity over the course of a week, the compliance module 117 can be operable to determine, at 240, if the user is on track to meet the target goal for the week.

In some instances, determining compliance with the training regimen, at 240, can include determining if the user is exercising near the top of the prescribed training zone. For example, if the training regimen calls for the user to currently be exercising in zone 2, the compliance module 117 can determine how close the user is to the aerobic threshold, and can encourage the user to exercise with an intensity that approaches, but does not exceed, the aerobic threshold.

At 250, feedback can be provided, in real time and/or substantially continuously, based on compliance or non-compliance with the training regimen. For example, the comparison module 117 can be operable to send a signal to the output module 118 such that an output device alerts the user to compliance status. For example, the user can be encouraged to increase intensity of a physical activity if the current activity intensity is below the intensity prescribed by the training regimen, decrease intensity if the current activity intensity is above the intensity prescribed by the training regimen, encourage the user to maintain an intensity if the current activity is within the target intensity, notify the user of progress towards a goal (e.g., "5 more minutes at this intensity"), and so forth. In some instances, feedback to increase an intensity of an exercise can be provided, at 250, until the compliance module 117 indicates that the user has left the prescribed zone. Additional feedback can then be prescribed, at 250, to slightly decrease intensity. In this way, in some instances, the user can be encouraged to exercise at the top of the prescribed zone.

In some instances, compliance with the training regimen can be determined, at 240, and feedback can be provided, at 250, based solely on lactate concentration. In other instances, compliance with the training regimen can be determined, at 240, and feedback can be provided, at 250, based on any number of parameters, such as lactate concentration, heart rate, respiration, galvanic skin response, altitude, duration of an activity, terrain (hills), etc.

Any suitable feedback can be provided at 250. For example, musical cues can encourage a user to increase, decrease, or maintain an intensity by varying the tempo, volume, frequency, etc. of a composition. Visual cues, such as stop-light style displays can be presented to encourage a user to maintain or alter an intensity of an activity. Charts, graphs, or other data visualization can provide feedback. Spoken phrases, such as "speed up," "slow down," "begin sprint," "begin recovery from sprint," "5 more minutes at this intensity," "you're doing great," "you've done better," "just a little faster," and so forth, can be provided. Haptic feedback, such as metronomic pulsing can be provided.

In some instances, feedback can be provided based on challenges responsive to difficulties commonly experienced by athletes engaging in the type of training regimen defined, at 210. For example, in the initial stages of zone training, optimal training may be lower intensity than the user may be accustomed; a challenge can be intended to inform the user to decrease intensity. In other instances, challenges can be customized or selected for a user based on, for example, personal preferences, training regimen, etc. Feedback can be stored and/or tagged (e.g., in a database) by type and/or the desired effect—for instance for encouragement or to more directly challenge.

Feedback can be provided, at 250, based on preselected or preferences of the user. For example, the user can preselect along a spectrum of his or her desired ratio of positive versus negative reinforcement to which he or she responds. Coaching feedback can be probabilistically selected according to these ratios. Users can vote on their favorite sayings. For example, an up vote can increase the probability that a motivational message will be repeated, while a down vote can decrease the probability that the motivational message will be repeated, and/or to reject the message from being appearing in the future.

In some instances, feedback can be provided, at 250, after a training activity in addition or alternative to real-time feedback. For example, a workout summary can be presented at the conclusion of and/or during an exercise, such as the example workout summary shown in FIG. 4. Historic workout data can be used to predict performance for a future workout or event, to establish pacing, analyze progress. Historic data can further be used to detect deviations from past performance, for example during a workout. For instance, if a user is unable to maintain a pace that he or she has previously set, it can be an indication of a mental lapse. Feedback can be provided to the user in the event such a deviation occurs encouraging the user to increase his or her pace. If the user does not increase his or her pace, it can be an early indication of injury or overtraining, and training regimens can be adjusted and/or redefined.

In some instances, during or at the conclusion of a workout, training regimes can be updated or defined for future workout sessions based on the user's performance and/or compliance with the training regimen defined at 210. For example, if a workout is completed with a high degree of compliance to the prescribed regimen, in some instances, a more challenging workout can be defined for a future session. Conversely, if a workout is completed with a low degree of compliance to the prescribed regimen, a less challenging workout can be defined for a future session. As another example, after a low-intensity, long-duration exercise is completed, long-term training regimen can be updated such that the next workout includes speed work or intervals such that the long term training regimen includes a variety of different exercises targeting different muscle adaptations.

While various embodiments have been described herein, it should be understood that they have been presented by way of example only, and not limitation. For example, although some embodiments described herein relate to providing feedback to a user while the user exercises, in other embodiments, feedback can be provided to a coach, trainer, and/or other individual. Furthermore, although embodiments are generally described within the context of a human athlete being monitored and provided feedback, it should be understood that that systems, methods, and apparatus described herein can be applied to any mammalian animal. For example, lactate of a racing greyhound can be detected and real-time and/or post-workout feedback can be provided to trainer. The trainer can encourage the dog to increase and/or decrease its pace (e.g., increase or decrease the speed of a lure) based on lactate concentration.

As another example, although embodiments generally describe providing training feedback based on lactate concentration, it should be understood that such training feedback may be based on any suitable data. That is, the training device 110 and/or sensor 120 can be operable to detect and/or provide feedback based on any suitable physiological or other feature. For example, the sensor 120 can be operable to measure heart rate, respiration rate, galvanic response, etc. The training device 110 may store or have access to GPS data, map data, past activity data, sleep data, diet information, travel information, etc. Such data can be combined in any suitable fashion to provide feedback. As an example, the training device 110 can be operable to detect that the user is approaching a hill based on GPS and/or map data. The training device 110 can encourage the user to conduct a hill sprint based on such information. Alternatively, the training device 110 may encourage the user to conserve energy leading up to a hill based on, for example, the user's heart rate being higher than the user's heart rate has been in the past leading up to the hill.

Furthermore, although various embodiments have been described as having particular features and/or combinations of components, other embodiments are possible having a combination of any features and/or components from any of embodiments where appropriate as well as additional features and/or components.

Where methods described herein indicate certain events occurring in certain order, the ordering of certain events may be modified. Additionally, certain of the events may be performed repeatedly, concurrently in a parallel process when possible, as well as performed sequentially as described above. Furthermore, certain embodiments may omit one or more described events. Where methods are described, it should be understood that such methods can be computer-implemented methods. Similarly stated, a non-transitory processor readable medium can store code representing instructions configured to cause a processor to cause the described method to occur or be carried out.

Some embodiments described herein relate to computer-readable medium. A computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, PLDs, ROM and RAM devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

What is claimed is:

1. A non-transitory processor readable medium storing code representing instructions to be executed by a processor, the code comprising code to cause the processor to:

receive, from a non-invasive sensor, a signal associated with a direct measurement of a concentration of lactate in a blood stream of a mammalian body;

determine a ratio of aerobic to anaerobic exertion based on the direct measurement of the concentration of lactate;

compare the ratio of aerobic to anaerobic exertion to an aerobic threshold and an anaerobic threshold; and send a signal to an output device to cause the output device to provide feedback during a training activity based on a proximity of the ratio of aerobic to anaerobic exertion to at least one of the aerobic threshold or the anaerobic threshold.

2. The non-transitory processor readable medium of claim 1, wherein the feedback includes an instruction to the user to reduce an intensity of a physical activity based on the ratio of aerobic to anaerobic exertion exceeding the aerobic threshold.

3. The non-transitory processor readable medium of claim 1, wherein:

the ratio of aerobic to anaerobic exertion is determined based solely on the direct measurement of the concentration of lactate; and the feedback includes an instruction to the user to reduce an intensity of a physical activity based solely on the comparison of the ratio of aerobic to anaerobic exertion to the aerobic threshold and the anaerobic threshold.

4. The non-transitory processor readable medium of claim 1, wherein the non-invasive sensor is a first non-invasive sensor and concentration of lactate is a first physiological parameter, the code further comprising code to cause the processor to:

receive, from a second non-invasive sensor, a signal associated with a second physiological parameter different from the first physiological parameter, the code to cause the processor to determine the ratio of aerobic to anaerobic exertion includes code to cause the processor to determine the ratio of aerobic to anaerobic exertion based on the direct measurement of the concentration of lactate and the second physiological parameter.

5. The non-transitory processor readable medium of claim 1, wherein the feedback includes an instruction to increase an intensity of a physical activity based on the concentration of lactate.

6. The non-transitory processor readable medium of claim 1, wherein the ratio of aerobic to anaerobic exertion is determined based solely on the direct measurement of the concentration of lactate.

7. The non-transitory processor readable medium of claim 1, wherein the ratio of aerobic to anaerobic exertion is a first ratio, the code further comprising code to cause the processor to:

define a training regimen prescribing performing a physical activity performed at a first intensity level for a first duration and the physical activity performed at a second intensity level for a second duration, the first intensity level being below the aerobic threshold and associated with a second ratio of aerobic to anaerobic exertion associated with oxygen uptake, the second intensity level being below the anaerobic threshold and associated with a third ratio of aerobic to anaerobic exertion lower than the second ratio, the third ratio associated with high intensity endurance; and record the first ratio and a third duration associated with the first ratio.

8. The non-transitory processor readable medium of claim 7, the code further comprising code to cause the processor to:

send a signal to the output device to cause the output device to present an instruction to reduce an intensity of the physical activity based on the first ratio being less than the second ratio and the third duration being greater than the first duration.

9. The non-transitory processor readable medium of claim 1, wherein the ratio of aerobic to anaerobic exertion is a first ratio, the code further comprising code to cause the processor to:

define, at a first time, a training regimen prescribing: (1) performing a physical activity at a first intensity level associated with a second ratio of aerobic to anaerobic exertion, the second ratio of aerobic to anaerobic exertion being below the aerobic threshold, (2) performing the physical activity at a second intensity level associated with a third ratio of aerobic to anaerobic exertion, the third ratio of aerobic to anaerobic exertion being above the first ratio of aerobic to anaerobic exertion and below the anaerobic threshold, and (3) avoiding performing the physical activity at a third intensity level between the first intensity level and the second intensity level, the signal associated with the direct measurement of the concentration of lactate received at a second time after the first time; and send, after a completion of the physical activity, a signal to the output device to cause the output device to present an indication of compliance with the training regimen.

10. The non-transitory processor readable medium of claim 1, wherein the ratio of aerobic to anaerobic exertion is a first ratio, the code further comprising code to cause the processor to:

define, at a first time, a training regimen prescribing (1) performing a physical activity at a first intensity level associated with a second ratio of aerobic to anaerobic exertion below the aerobic threshold, (2) performing the physical activity at a second intensity level associated with a third ratio of aerobic to anaerobic exertion above the aerobic threshold and below the anaerobic threshold, and (3) avoiding performing the physical activity at a third intensity level between the first intensity level and the second intensity level, the signal associated with the direct measurement of the concentration of lactate received at a second time after the first time; and send a signal to the output device to cause the output device to provide feedback to alter an intensity of the physical activity based on the ratio of aerobic to anaerobic exertion determined based on the direct measurement of the concentration of lactate being associated with the third intensity level.

11. The non-transitory processor readable medium of claim 1, wherein the code to cause the processor to determine the ratio of aerobic to anaerobic exertion includes code to cause the processor to determine the ratio of aerobic to anaerobic exertion substantially continuously during a performance of a physical activity based on the signal being received from the non-invasive sensor substantially continuously.

12. The non-transitory processor readable medium of claim 1, wherein the ratio of aerobic to anaerobic exertion is a first ratio, the code further comprising code to cause the processor to:

define a training regimen prescribing performing a physical activity at an intensity level associated with a second ratio, the second ratio being less than the first ratio, the feedback including an instruction to increase an intensity of a physical activity to approach the intensity level without exceeding the intensity level.

13. The non-transitory processor readable medium of claim 1, wherein the ratio of aerobic to anaerobic exertion is a first ratio determined during a first time period, the code further comprising code to cause the processor to:
define a training regimen prescribing (i) performing a physical activity at a first intensity level associated with a second ratio below the aerobic threshold during the first time period and (ii) performing the physical activity at a second intensity level associated with at a third ratio greater than the second ratio during a second time period,
the feedback including an instruction to increase an intensity of the physical activity to approach the first intensity level without exceeding the first intensity level.

14. The non-transitory processor readable medium of claim 1, wherein the ratio of aerobic to anaerobic exertion is a first ratio received during a second time period, the code further comprising code to cause the processor to:
define a training regimen prescribing (i) performing a physical activity at a first intensity level associated with a second ratio below the aerobic threshold during a first time period and (ii) performing the physical activity at a second intensity level associated with a third ratio greater than the second ratio during the second time period,
the feedback including an instruction to increase an intensity of the physical activity.

15. The non-transitory processor readable medium of claim 1, wherein the signal associated with the direct measurement of the concentration of lactate is from a plurality of signals representing a plurality of direct measurements of the concentration of lactate, the code further comprising code to cause the processor to:
define the aerobic threshold based on a first inflection point in the plurality of direct measurements of the concentration of lactate; and
define the anaerobic threshold based on a second inflection point in the plurality of direct measurements of the concentration of lactate.

16. The non-transitory processor readable medium of claim 1, wherein the signal associated with the direct measurement of the concentration of lactate is a first signal associated with a first direct measurement of a first concentration of lactate from a plurality of signals representing a plurality of direct measurements of the concentration of lactate, the code further comprising code to cause the processor to:
define the aerobic threshold based on a first inflection point in the plurality of direct measurements of the concentration of lactate; and
define the anaerobic threshold based on a second inflection point in the plurality of direct measurements of the concentration of lactate, the ratio of aerobic to anaerobic exertion determined based on the first concentration of lactate relative to at least one of the aerobic threshold and the anaerobic threshold.

17. The non-transitory processor readable medium of claim 1, wherein the signal associated with the direct measurement of the concentration of lactate is a first signal associated with a first direct measurement of a first concentration of lactate from a plurality of signals representing a plurality of direct measurements of the concentration of lactate, the code further comprising code to cause the processor to:
define the aerobic threshold based on a first inflection point in the plurality of direct measurements of the concentration of lactate; and
define the anaerobic threshold based on a second inflection point in the plurality of direct measurements of the concentration of lactate, the ratio of aerobic to anaerobic exertion determined based on the first concentration of lactate relative to the aerobic threshold and the anaerobic threshold.

18. The non-transitory processor readable medium of claim 1, wherein:
the signal associated with the direct measurement of the concentration of lactate is from a plurality of signals representing a plurality of direct measurements of the concentration of lactate; and
the ratio of aerobic to anaerobic exertion is a first ratio, the code further comprising code to cause the processor to:
define the aerobic threshold based on a first inflection point in the plurality of direct measurements of the concentration of lactate;
define the anaerobic threshold based on a second inflection point in the plurality of direct measurements of the concentration of lactate; and
define a training regimen prescribing: (1) performing a physical activity at a first intensity level that does not exceed the aerobic threshold, (2) performing the physical activity at a second intensity level that does not exceed the anaerobic threshold, and (3) avoiding performing the physical activity at a third intensity level that exceeds the aerobic threshold and is below the second intensity level.

19. An apparatus, comprising:
an input module configured to be communicatively coupled to a sensor configured to directly and non-invasively measure a lactate concentration in a blood stream of a mammalian body during a physical activity;
a training module communicatively coupled to the input module, the training module configured to calculate an exertion level based on the direct and non-invasive measurement of lactate concentration;
a comparison module configured to compare the lactate concentration to an aerobic threshold; and
an output module communicatively coupled to the training module and the comparison module, the output module configured to cause an output device to provide training feedback during the physical activity based on the comparison of the lactate concentration to the aerobic threshold.

20. The apparatus of claim 19, wherein the training module is configured to calculate the exertion level based solely on the concentration of lactate.

21. The apparatus of claim 19, wherein the training module is configured to calculate the exertion level independently of a heart rate of the mammalian body.

22. The apparatus of claim 19, wherein the comparison module is configured to compare the lactate concentration to the aerobic threshold and an anaerobic threshold.

23. The apparatus of claim 19, wherein the apparatus is configured to be coupled to the mammalian body during the physical activity such that the input module receives a signal from the sensor while the apparatus is coupled to the mammalian body and the output module causes the output device to provide training feedback while the apparatus is coupled to the mammalian body.

24. The apparatus of claim 19, wherein the comparison module is configured to classify the exertion level as being within a first training zone, a second training zone, or a third training zone based on the direct and non-invasive measurement of lactate concentration, the first training zone associated with a first ratio of aerobic to anaerobic exertion below the aerobic threshold, the third training zone associated with a third ratio of aerobic to anaerobic exertion above the aerobic threshold and below an anaerobic threshold, and the second training zone associated with a second ratio of aerobic to anaerobic exertion between the first ratio and the third ratio.

25. The apparatus of claim 19, wherein:
the training module is configured to define the aerobic threshold based on a first inflection point in the lactate concentration;
the training module is configured to define an anaerobic threshold based on a second inflection point in the lactate concentration;
the comparison module is configured to classify the exertion level as being within a first training zone, a second training zone, or a third training zone based on the direct and non-invasive measurement of lactate concentration, the first training zone associated with a first ratio of aerobic to anaerobic exertion below the aerobic threshold, the third training zone associated with a third ratio of aerobic to anaerobic exertion above the anaerobic threshold, and the second training zone associated with a second ratio of aerobic to anaerobic exertion that exceeds the aerobic threshold and is below the third ratio; and
the output module is configured to cause the output device to provide training feedback to avoid the second training zone when the comparison module classifies the exertion level within the second training zone.

26. A method, comprising:
defining, with a training aid and during a first time period, a training regimen prescribing (1) performing a physical activity performed at a first intensity level associated with a first lactate concentration, (2) performing the physical activity at a second intensity level associated with a second lactate concentration, and (3) avoiding performing the physical activity at a third intensity level associated with a third lactate concentration, the third lactate concentration being between the first lactate concentration and the second lactate concentration;
classifying, at the training aid and during a second time period in which a user is engaged in the physical activity, the second time period after the first time period, a training zone for the physical activity based on a measured lactate concentration;
determining, during the second time period, that the training zone is associated with the third intensity level; and
sending a signal to an output device to cause the output device to provide a prompt to the user to alter the performance of the physical activity during the second time period to avoid the third intensity level.

27. The method of claim 26, wherein the second time period has a duration of less than thirty minutes.

28. The method of claim 26, further comprising:
receiving, during the second time period and before classifying the training zone, a signal from a non-invasive sensor associated with a direct measurement of the measured lactate concentration.

29. The method of claim 26, wherein the measured lactate concentration is a first measured lactate concentration, the training zone is a first training zone, and the prompt is a first prompt to perform the physical activity at the first intensity level, the method further comprising:
receiving, during the second time period and after sending the signal to the output device, a signal from a non-invasive sensor associated with a second measured lactate concentration;
classifying, at the training aid and during the second time period, a second training zone for the physical activity based on the second measured lactate concentration;
determining that the second training zone is a target training zone; and
sending a signal to the output device to cause the output device to provide a second prompt to maintain a second intensity of the physical activity.

30. The method of claim 26, wherein the measured lactate concentration is a first measured lactate concentration and the training zone is a first training zone, the method further comprising:
receiving, during the second time period, a signal from a non-invasive sensor associated with a second measured lactate concentration, the second measured lactate concentration associated with the first intensity level;
classifying, at the training aid and during the second time period, a second training zone for the physical activity based on the second measured lactate concentration;
determining that the second training zone is a target training zone; and
sending a signal to the output device to cause the output device to display a timer counting down a duration while the signal associated with the second measured lactate concentration is received.

31. The method of claim 26, wherein the measured lactate concentration is a first measured lactate concentration, the training zone is a first training zone, and the training regimen prescribes performing the physical activity at the first intensity level for a first duration and performing the physical activity at a second intensity level for a second duration, the method further comprising:
receiving during a third time period, a signal from a non-invasive sensor associated with a second measured lactate concentration;
classifying, at the training aid and during the third time period, a second training zone for the physical activity based on the second measured lactate concentration, the second training zone associated with the first intensity level;
determining during the third time period that the physical activity has been performed for the first duration; and
sending a signal to the output device to cause the output device to prompt the user to alter the performance of the physical activity to conform with the second intensity level based on determining that the physical activity has been performed for the first duration.

32. The method of claim 26, wherein the first lactate concentration is associated with a ratio of aerobic to anaerobic exertion below an aerobic threshold and the second lactate concentration is associated with a ratio of aerobic to anaerobic exertion above an anaerobic threshold, the method further comprising:
directly and non-invasively measuring the measured lactate concentration.

33. The method of claim 26, wherein the measured lactate concentration is a first measured concentration from a plurality of measured lactate concentrations, the method further comprising:
directly non-invasively measuring a plurality of measured lactate concentrations including the measured lactate concentration;

defining an aerobic threshold based on a first inflection point in the plurality of measured lactate concentrations;

defining an anaerobic threshold based on a second inflection point in the plurality of measured lactate concentrations, the first lactate concentration approaching but not exceeding the aerobic threshold, the second lactate concentration approaching but not exceeding the anaerobic threshold, and the third lactate concentration exceeding the aerobic threshold.

* * * * *